United States Patent [19]

Sakai et al.

[11] Patent Number: 5,316,633
[45] Date of Patent: May 31, 1994

[54] METHOD AND APPARATUS FOR MEASURING SENSITIZATION OF STRUCTURAL MEMBERS

[75] Inventors: Masanori Sakai, Hitachi; Noriyuki Ohnaka, Katsuta; Masakiyo Izumiya, Mito; Shigeo Hattori, Ibaraki, all of Japan

[73] Assignee: Hitachi, Ltd., Tokyo, Japan

[21] Appl. No.: 916,692

[22] Filed: Jul. 22, 1992

[30] Foreign Application Priority Data

Jul. 23, 1991 [JP] Japan .................................. 3-205632

[51] Int. Cl.$^5$ ...................... G01N 27/26; G21C 17/00
[52] U.S. Cl. .................. 204/153.11; 204/404; 376/245; 376/249; 376/305; 422/9
[58] Field of Search .................. 204/153.11, 404; 210/85, 739, 746, 749, 759; 422/9–10; 376/249, 245, 305

[56] References Cited

U.S. PATENT DOCUMENTS

| | | | |
|---|---|---|---|
| 4,179,349 | 12/1979 | Park | 204/404 |
| 4,564,436 | 1/1986 | Buzzanca et al. | 204/400 |
| 4,937,038 | 6/1990 | Sakai et al. | 376/245 |

OTHER PUBLICATIONS

"Method of Electrochemical Potentiokinetic Reactivation Ratio Measurement for Stainless Steels" By Japanese Industrial Standard JIS GO 580 (1986).
"Electrochemical Methods Fundamentals and Applications" By: Allen J. Bard, Larry R. Faulkner, pp. 176–207.
Subcommittee 63-2 of Boshoku Kyokai in a report published in "Boshoku Gijyutsu (Anti–corrosion Technology)" vol. 39, No. 11, 1990, pp. 641–652.
The 33rd discussion on anticorrosion held in Nagano 1990 spondored by Fushoku Boshoku Kyokai, a lecture No. C-201.

*Primary Examiner*—Aaron Weisstuch
*Attorney, Agent, or Firm*—Antonelli, Terry, Stout & Kraus

[57] ABSTRACT

A method and system for electrochemically measuring the sensitization to stress corrosion cracking of small pipes of plant structural members in a very short period of time. A micro electrochemical cell for measuring the sensitization is movably disposed within a BWR plant ICM housing or an instrumentation pipe. An electrochemical instrumentation system for performing the electrochemical potential variation such as pulse voltammetry and a remote control system for remotely controlling the electrochemical cell are provided.

18 Claims, 9 Drawing Sheets

METHOD AND APPARATUS FOR MEASURING SENSITIZATION OF STRUCTURAL MEMBERS

BACKGROUND OF THE INVENTION

The present invention relates to a method of measuring the sensitization of a structural material of a plant and a system for the same, and, in particular to a method of plant operation management based upon a sensitization measuring method concerned with the intergranular stress corrosion cracking susceptibility of a plant structural member made of, for example, a stainless steel. The present invention can be applied in any field where monitoring of the intergranular stress corrosion cracking of a structural member due to sensitization is possible, e.g. a thermal power generating plant and a chemical plant.

Methods of measuring the sensitization have recently been compiled by a subcommittee 63-2 of Boshoku Kyokai in a report published in "Boshoku Gijyutsu (Anti-corrosion technology), Vol. 39 N. 11, 1990). Among these prior art methods, a non-destructive sensitization measuring method of the type into which the method of the present invention is classified is described in "A method of measuring the electrochemical reactivation rate of stainless steel", Japanese Industrial Standard JIS GO 580 (1986). This technique is generally referred to as EPR 25 (Electrochemical Potentiokinetic Reactivation) method. The nondestructive electrochemical sensitization measuring method is classified into this EPR method. In this method anode polarization is performed measuring method is classified into this EPR method. In this method, anode polarization is performed starting from the natural electrode potential. Immediately after reaching +0.3V using a saturated calomel reference electrode, the potential is swept in an opposite direction. After reactivation, the sweeping is terminated at a potential at which the anode current again becomes zero.

The result is determined by the following formula. The value is rounded to the first decimal place according to JIS Z 8401.

Reactivation rate (%)=(maximum anode current density in active mode in the forward path) / (maximum anode current density in active mode in the return path)×100.

In the EPR method, the amount of sample liquid and the potential sweeping speed are prescribed as not less than 200 ml and 100±5 mV/min, respectively. Accordingly, reduction in size of the electrochemical cell is limited to 200 ml in these conditions.

In the 33rd discussion on anticorrosion held in Nagano, Japan in 1990 and sponsored by Fushoku Boshoku Kyokai, lecture No. C-201 reports that an increase in anticorrosion current from the grain boundary apparently becomes higher than that in grains by irradiation with a laser beam. However, in this report, the relation between the irradiation with a laser beam and the sensitization of a member has not been studied.

There are a number of scientific literature publications on electrochemical pulse instrumentation. "Electrochemical Methods" published by John Wiley & Sons, Inc. (1980), pp 176 to 206 mainly describe principles of reverse pulse, normal pulse, and differential pulse voltammetry in detail. Concerning the square wave voltammetry, quantitative analysis techniques using peak area are reported in Analytical Chemistry, Vol. 36, pp 420 to 424 (1987). However, pulse voltammetry has heretofore been studied from the aspect of an electrical analysis technique of a very small amount of metal ions and as an analysis technique of electrochemical reaction mechanisms. There has been no study to detect the sensitization of structural elements using these pulse voltammetric instrumentation techniques for the management of plant operation. There has been no report that the sensitization of structural members can be detected by using the pulse voltammetric measuring technique.

It is preferable to execute the pulse voltammetry in a pulse mode. In the examples of the present invention which will be described hereafter, normal pulse voltammetry and differential pulse voltammetry give excellent results.

The pulse voltammetry which can be performed in accordance with the present invention includes normal pulse voltammetry, reverse pulse voltammetry, differential pulse voltammetry, differential normal pulse voltammetry, square wave pulse voltammetry, etc.

SUMMARY OF THE INVENTION

The prior art has not solved the technical problems in measurement associated with using a micro electrochemical cell and has a problem in that the intergranular stress corrosion susceptibility of a plant structural member cannot be evaluated by flexible nondestructive sensitization measuring of an object to be monitored, such as inside small pipes.

It is an object of the present invention to provide a method of measuring the sensitization of an object to be monitored, such as the inside of small pipes which are hardly accessible by the prior art electrochemical methods, so as to evaluate the intergranular stress corrosion susceptibility of plant structural members while maintaining the safety (this term will be used herein to mean that no intergranular stress corrosion will occur) of the structural members.

It is another object of the present invention to provide a water quality control system for a nuclear power plant by measuring the sensitization of structural members of the nuclear power plant.

It is a further object of the present invention to provide a preventive safety system for predicting an accident in a cooling system such as leakage of coolant in a core by measuring the sensitization of the structural members of a nuclear power plant and comparing the measurement result with a reference value.

In order to accomplish the above mentioned objects, the present invention provides a method of electrochemically measuring the sensitization of a structural member corresponding to the intergranular stress corrosion cracking susceptibility of the plant structural member comprising the steps of: applying a series of potential pulse signals from an electrochemical measuring system to a structural member within an electrochemical cell in an object to be monitored for a period of time; measuring a current generated by the electrochemical reaction of the structural member in the object to monitored due to application of each potential pulse signal; and determining the sensitization of the structural member corresponding to the intergranular stress corrosion cracking susceptibility of the plant structural member in accordance with an obtained current-potential curve.

The present invention further provides a method of electrochemically measuring the sensitization of a structural member corresponding to the intergranular stress corrosion cracking susceptibility of the plant structural member in an object to be measured, comprising the steps of: applying a series of potential pulse signals from an electrochemical measuring system to a structural member within an electrochemical cell in an object to be monitored for a period of time; measuring a current generated by the electrochemical reaction of the structural member in the object to monitored due to application of each potential pulse signal; and determining the sensitization of the structural member corresponding to the intergranular stress corrosion cracking susceptibility of the plant structural member in accordance with the relation with charge passed in electrolysis (Coulomb number).

In the above mentioned method of measuring the sensitization of a plant structural member, the potential pulse signal is a potential signal in a pulse voltammetric mode which is selected from a normal pulse, a square wave, a differential pulse, and a reverse pulse. The relation to the current-potential curve is obtained by comparing a peak current value on a current potential curve which is obtained when the potential is swept in a noble or anodic direction from a starting potential of a series of pulse potential signals including the pulse voltammetry, or a charge passed in electrolysis (Coulomb number) until a preset potential of the current-potential curve is reached, or a current value at a potential in interest on the current-potential curve is reached with at least one of the current value on the current-potential curve of a sensitized member which is a predetermined reference, or the charge passed in electrolysis (Coulomb number) or the current value at said potential.

The relation of the current-potential curve is obtained by comparing at least one of the ratio of the peak current values corresponding to the current-potential curves which are obtained when the potential is swept in noble and base directions from a starting potential at which a series of pulse potential signals including the pulse voltammetry are applied, the ratio of current values on the current-potential curves in respective sweeping directions at potentials in interest, and the ratio of the charges passed in electrolysis (Coulomb number) corresponding to respective current-potential curves obtained by respective pulse potential sweeping in noble and base directions with one of the ratio of peak current values obtained from a sensitized material chosen as a predetermined reference, the ratio of current values of the current-potential curves in respective sweeping directions at a potential in interest, and the ratio of charges passed in electrolysis corresponding to the current-potential curves in respective sweeping directions.

In the method of measuring the sensitization of the present invention, the electrochemical cell nay include an on-line monitoring mechanism for which it is necessary to position the electrochemical cell in an object to be monitored, an operation control mechanism using a magnetic force or a vacuum control mechanism, a remote control operating unit, conduits for charging or discharging a measuring electrolyte and a liquid for washing the object after measurement, and a remote control system for positioning said electrochemical cell in the object to be monitored.

The electrochemical measuring system is capable of repeatedly sweeping the pulse potential in noble and base directions from a starting potential at which a series of pulse potential signals including pulse voltammetry are applied and includes a system which is capable of measuring the charge passed in electrolysis or automatically reading the current value on a current-potential curve at a preset potential to display measured data on a CRT or to output data.

As the electrolyte, sulfuric acid, a solution of sulfuric acid and potassium thiocyanate, oxalic acid, a solution of sulfuric acid and ferric sulfate, a solution of sulfuric acid and copper sulfate, nitric acid, hydrochloric acid, acetic acid, and a solution of sulfuric acid and sodium sulfate may be used.

The present invention provides a plant operation management method in which the safety of plant structural members is evaluated by measuring the sensitization of structural members by using the above mentioned method of the present invention.

The technique to measure the sensitization corresponding to the intergranular stress corrosion susceptibility of a structural member when the plant operation is regularly checked is related to evaluation of the reliability of the member per se. A result of evaluation of the sensitization of an object to be monitored is directly related with the operation evaluation schedule in an aspect of plant safety. In order to maintain the safety of operating plants, technology has been required in which a field test of an object to be monitored in a wide range can be performed and evaluation of the safety of the object can be quickly obtained.

Such a technology includes three technical requirements as follows:

1) measurement and evaluation of very small areas, for example, in small pipes;

2) inspection of a wide range of objects to be monitored in a short period of time; and 3) remote scanning capability.

The three technical problems have been solved as as follows: Design of a micro electrolytic cell for electrochemical measurement is necessary to make it possible to perform measurements in small pipes and the like. To this end, a technique is necessary which makes it possible to decrease the charge passed through an electrochemical cell in order to reduce the amount of generated gas as much as possible and to measure the sensitization of an object to be monitored. The present invention has solved this problem by the pulse electrochemical measurement by using pulse voltammetry. It is easy to decrease the charge passed to an electrochemical cell to $1/10^4$ of that in the usual electrochemical measurement in a steady state at the usual scanning speed if a potential pulse having a pulse width of about 1 second or shorter, particularly 1 to 50 m sec is used. Field tests can be conducted in such a condition that the change in the state of the uppermost surface of the structural member caused by the examination of an object to be monitored is substantially negligible.

If the measuring conditions are preset so that the pulse width is 20 m sec and the number of pulses in one scanning is 20 in the normal mode of the pulse voltammetry, the period of time for which a current flows through an electrochemical cell during the measurement is only 0.4 sec. If the measurement of @he sensitization is conducted by the electrochemical measurement of the charge passed in electrolysis which is $1/10^4$ of that of the steady measurement, the necessary amount of the electrolyte may be simply calculated as $1/10^4$, similar to the case of the charge. It has been proved from the measurement of the current-potential curve using the pulse voltammetry that a high detection sensitivity can be obtained even on a current-potential current in a potential scanning area from a base to noble direction at which the sensitivity detection measurement is not in a steady state. This is due to the fact that the electrochemical response speed from a grain boundary in which a chromium depleted layer and chromium carbide layer, etc. are formed, i.e., the corrosion reaction speed of the grain boundary is higher than that of the grains, resulting in corrosion from the grain boundary being observed earlier than from the grains in a short interval of the pulse measuring period. Since the corrosion susceptibility of the grain boundary has a positive correlation with the sensitivity, the intergranular stress corrosion susceptibility can be detected by the pulse electrochemical measurement of the sensitization. Therefore, by performing the pulse electrochemical measurement, an electrochemical cell can be made smaller and the sensitization of structural members can be measured.

The second technical requirement, i.e. a rapid inspection technique, can be achieved by the pulse electrochemical measurement relying upon the pulse voltammetry which makes the measuring time shorter.

The third technical requirement requires a technique to remotely monitor an object to be monitored, a technique to two-dimensionally or three-dimensionally move an electrochemical cell along the surface of a structural member when the electrochemical cell is disposed on the object to be monitored, and a technique to fix the electrochemical cell on an object to be monitored to prevent the electrolyte from leaking from the electrochemical cell. In the present invention, these techniques are achieved by remotely controlling an on-line monitor sensor unit which is integrally formed on an electrochemical cell, an electromagnetic mechanism for fixing the cell, a vacuum cell component, and an electrochemical cell moving mechanism.

Electrochemical measurements based upon steady-state current-potential curve measurement have a problem in that the quality of the electrolyte is changed by the electrochemical decomposition of the electrolyte in the cell and the pressure inside the electrochemical cell is increased due to generation of gasses such as hydrogen gas because the measuring time is long. The reduction in size of the electrochemical cell is limited. If the scanning speed is simply increased by a so-called EPR method in which a usual potential signal is linearly scanned with respect to time, charging current predominantly flows to an electrical double layer existing at the interface between an object to be monitored and the electrolyte in an electrochemical cell, so that information on the sensitization will be generated in association with an increase in scanning speed. The pulse voltammetry is one of typical electrochemical measuring techniques which are capable of solving the problem of the charging current in the electrical double layer which is caused by the linear potential sweeping.

Among the various pulse voltammetry techniques, the normal pulse mode voltammetry having a capability of correcting for the charging current in the electrical double layer is inferior to those of the other differential pulse mode voltammetries and still has a problem of the charging current in a short time range such as several m sec to 10 m sec. Since the potential of the object to be monitored is returned to a sweep start position in which no polarization occurs after completion of each potential pulse of the normal pulse voltammetry, it is always possible to obtain correct sensitization information of the object to be monitored which is obtained at that pulse width. On the other hand, in the prior art technique of linearly sweeping the potential, the potential of the object to be monitored continuously changes from the start to the completion of the sweeping. The relation between the current-potential curve or a change in charge passed in electrolysis is complicated, whereby the evaluation analysis of the time parameter is generally harder than that in the normal pulse voltammetry. The reproducibility of data is low when the potential is linearly swept at a higher scanning speed. If the charge passed in the pulse electrochemical instrumentation in accordance with the present invention is considered, it is easy to measure the sensitization by using an electrochemical cell having an electrolyte of 1 $cm^3$ or less, or less, preferably 0.1 to 0.4 $cm^3$. This makes it possible to evaluate safety of plant structural members for managing the operation of a plant.

In a first aspect of the present invention, there is provided a method of electrochemically measuring the sensitization of a structural member corresponding to the intergranular stress corrosion cracking susceptibility of the plant structural member in an object to be measured, comprising the steps of: applying a series of potential pulse signals from an electrochemical measuring system to a structural member within an electrochemical cell located in an object to be monitored; measuring the current generated by the electrochemical reaction of the structural member in the object to monitored due to application of each potential pulse signal; and determining the sensitization of the structural member corresponding to the intergranular stress corrosion cracking susceptibility of the plant structural member in accordance with an obtained current-potential curve.

In a second aspect of the present invention, there is also provided a system for controlling the water quality in a coolant system of a nuclear power plant, comprising: an electrode housing for an electrolytic cell disposed on a structural member which is in contact with coolant, or a structural member of a reactor pressure vessel; a signal applying unit for applying a voltage-time waveform signal having a given parameter as a reference voltage of a reference electrode; a signal inputting unit for inputting a voltage-time waveform signal having a parameter determined by the kind of the voltammetry to said signal applying unit; a unit for storing in a memory a result of the voltammetry executed based upon the signal from said signal applying unit in accordance with the relation between the electrolytic current and the potential at which the electrolyzing current is obtained; a current determining unit for processing data stored in said storing unit to determine a current or peak current depending upon the kind of the voltammetry; an operating unit for determining the sensitization of said structural member based upon the determined current or peak current; and coolant control means for controlling the quality of said coolant based upon information from said operating unit.

DESCRIPTION OF THE PREFERRED EMBODIMENTS

The present invention will be described by way of embodiments with reference to the drawings.

Embodiment 1

Figure 1:
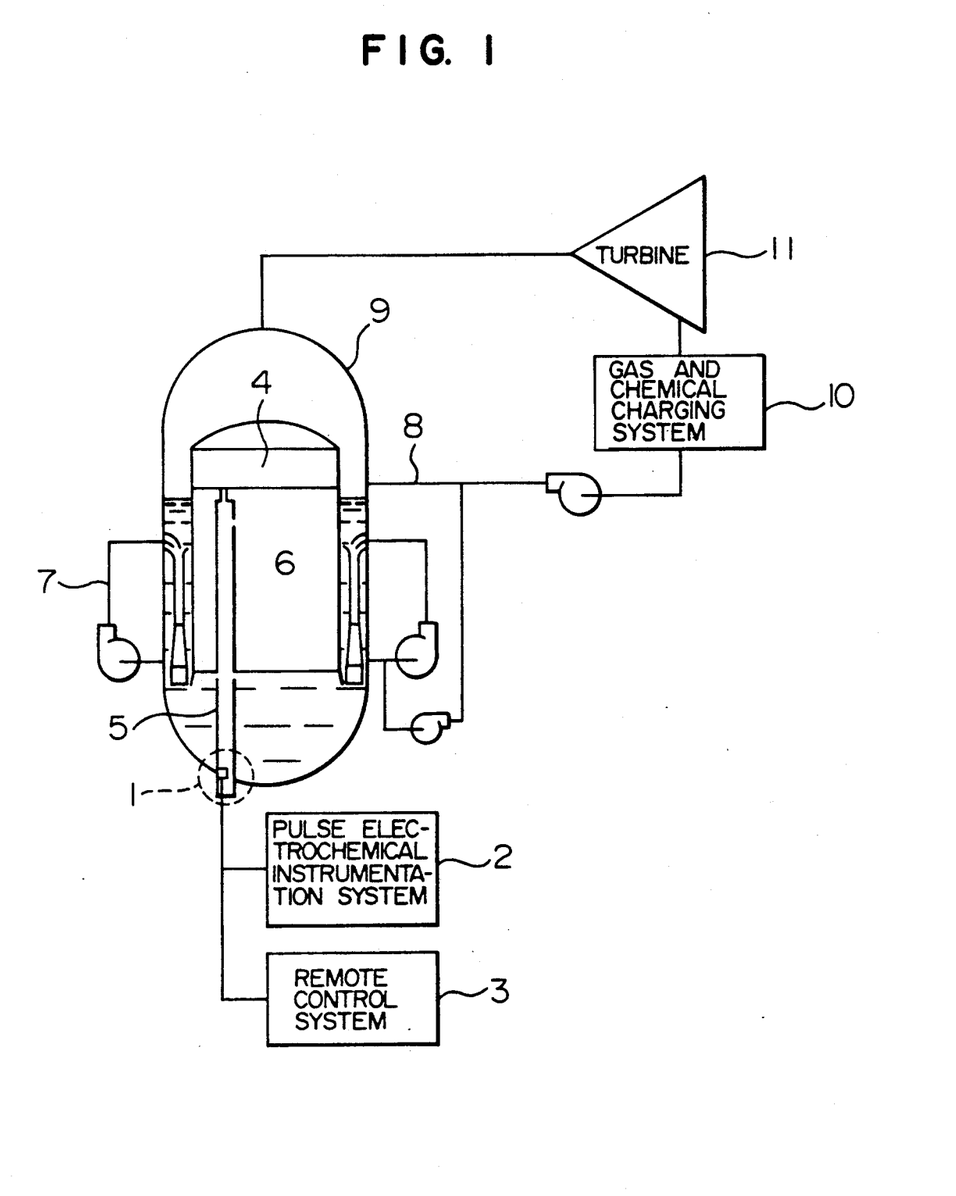
FIG. 1 is a schematic diagram showing a sensitization measuring system of the present invention which is used in an ICM housing of a nuclear power plant.
Figure 2:
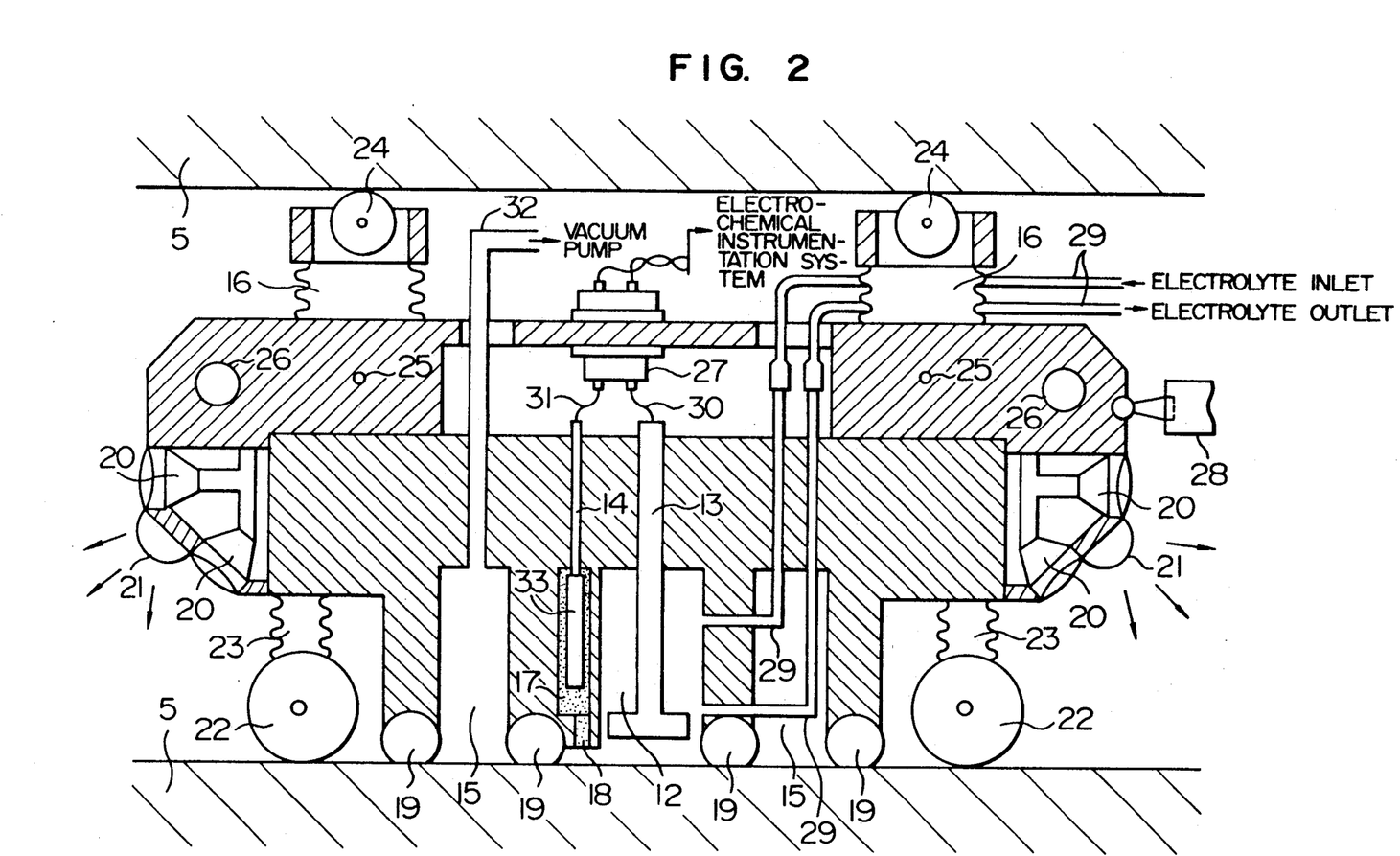
FIG. 2 is a schematic sectional view showing an electrochemical cell in the ICM housing of FIG. 1.

An embodiment in which the present invention is embodied in a BWR nuclear power plant is shown in FIG. 1. A micro electrochemical cell 1, shown in more detail in FIG. 2 is loaded in an ICM housing as shown in FIG. 1 and is connected with a pulse electrochemical instrumentation system 2 and a remote control system 3 for the micro electrochemical cell. Reference numeral 4 denotes a dryer; 5 denotes an in-core instrumentation pipe; 6 a core; 7 a reactor coolant recirculation system; 8 a reactor water supply pipe; 9 a reactor pressure vessel; 10 a gas and chemical charging system; and 11 a turbine.

In FIG. 2, the electrochemical instrumentation cell comprises a counter electrode 13 in an electrolyte reservoir 12 and a silver-silver chloride reference electrode 33 which is inserted into an agar material 17 containing 0.1 mole KCl and is connected with a silver conductor 14. The working electrode comprises the ICM housing, i.e. the inner surface of the in-core instrumentation pipe 5 bounded by rubber packings 19 which are in contact with the electrolyte reservoir 13. An electrolyte communicating passage between the electrolyte reservoir 13 and the silver-silver chloride reference electrode 33 is provided with a porous plug 18 made of ceramic. The counter electrode 13 is connected to a terminal of an detachable electrochemical measuring lead adapter 27 via a lead 30. The silver-silver chloride reference electrode 33 is connected with the other input of the adapter 27 via a silver conductor 14 and a lead 31. Both electrodes 13 and 33 are connected with the pulse electrochemical instrumentation system 2 via the adapter 27. The working electrode, i.e. the inner surface of the in-core instrumentation pipe 5 bounded by O-rings 19 is connected to a working electrode terminal of the pulse electrochemical instrumentation system 2 without passing through the adapter 27. Electrolyte charging and discharging pipes 29 are connected with the electrolyte reservoir 12 for charging and discharging the electrolyte to and from the reservoir 12. The electrochemical instrumentation system comprises a potentiostat, a function generator which is capable of generating pulse potential/time wave forms, and a computer system including a CRT, a recorder, a plotter, and a printer for directly controlling the pulse wave form from a system control CPU for processing data. An evacuation adjusting chamber 15 is connected with a vacuum pump via an evacuation control pipe 32. A piston mechanism 16 is linked with a pressure adjusting wheel 24 disposed above the piston. Reference numerals 20 and 21 denote a distal end of a fiber optic scope and a light source, respectively. Wheels 22 are linked with extendable wheel bearings 23 with springs. Reference numerals 25, 26, and 28 denote an exit through which a piston control pressure adjusting pipe is discharged, an exit through which wirings for the fiber optic scope and the light source are removed and an electrochemical cell positioning control terminal, respectively. As mentioned above, the leads of the counter and reference electrodes 13 and 14 respectively pass through the adapter 27 and are routed to the electrochemical instrumentation system 2. Leads from in-core structural members which are sample (working) electrodes are also connected with the instrumentation system 2. Since the structural member as a whole is grounded, the leads may be wired from any position of the pipes and the pressure vessel.

The electrochemical cell, all structural components of which are shown in FIG. 2, operates in the ICM housing as follows: The electrochemical cell can be moved along and within the in-core instrumentation pipe 5 and positioned in a desired position by wheels 22 and pressure adjusting wheels 24 via the electrochemical cell positioning control terminal 28 under control of the remote control system 3. At this time, the inner wall of the pipe 5 behind the electrochemical cell is illuminated by the light 21 so that the conditions inside of the pipe can be monitored by the front end 20 of the fiber optic scope. Accordingly, the electrochemical cell can be placed at an area to be monitored while the conditions within the pipe are detected by the remote control system 3. After the electrochemical cell has been positioned at an area to be monitored, the piston mechanism 16 is operated to increase the pressure in the chamber 15 until the rubber packings 19 are brought into contact with the inner wall surface in the vicinity of the area to be monitored. The evacuation degree in the evacuation chamber 15 is increased by the vacuum pump to such a level that the rubber packing 19 can perform a complete sealing function. After confirming from the evacuation degree that the electrochemical cell is closely contacted with the area to be measured, an electrolyte is charged into the reservoir 12 via pipes 29 which are under normal pressure and pulse electrochemical measurement of the area to be monitored which functions as an working electrode is started by using the pulse electrochemical instrumentation system 2. After completion of measurement, the electrolyte charging and discharging pipes 29 are connected with the vacuum pump system for discharging the electrolyte in the reservoir 12. Then, rinse water is circulated to the monitored area through the pipes 29. After sufficient rinsing with water, the pressure in the evacuation adjusting chamber 15 is returned to a normal pressure. This causes the rubber packings 19 to be separated from the monitored area by the biasing force of the springed wheel bearings 23 and the electrochemical cell to be returned to a stand-by state for the next measurement in which the cell can be moved and positioned in a desired position.

Figure 3:
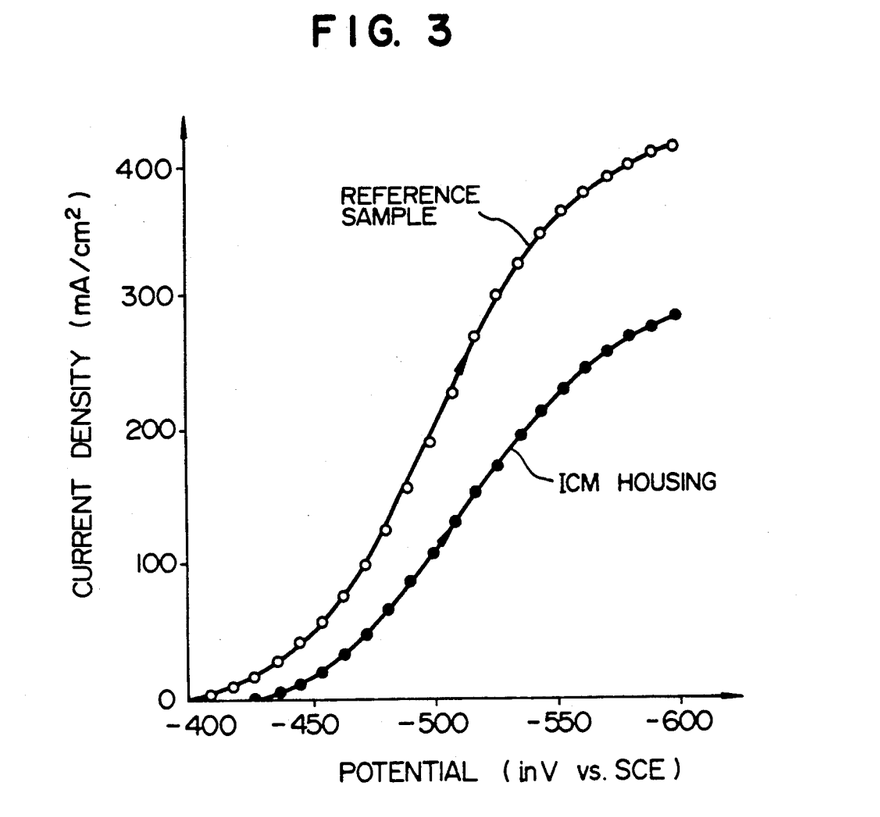
FIG. 3 is a normal pulse voltammogram in the ICM housing.
Figure 4:
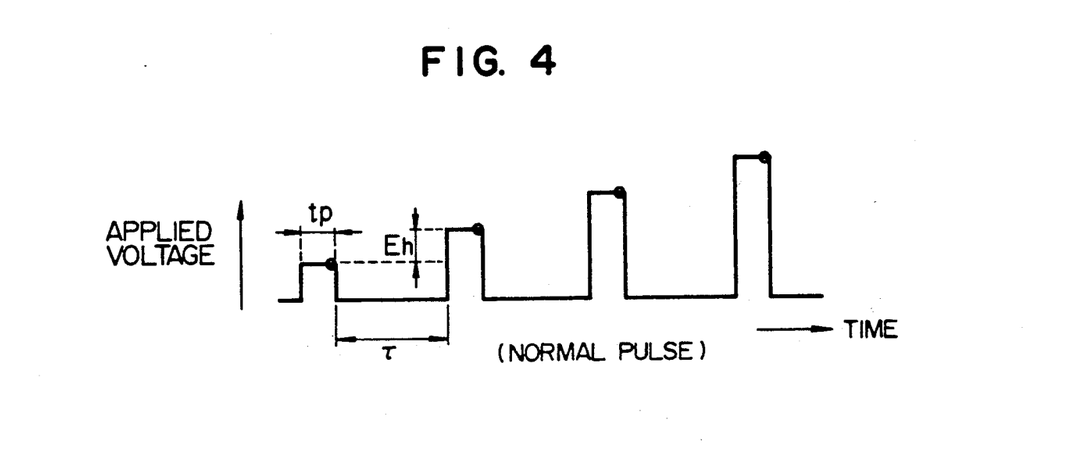
FIG. 4 is a wave form chart showing the relation between potential and time in the normal pulse voltammetry.

FIG. 3 is a normal pulse voltammogram (current-potential curve) in an ICM housing, which is measured in accordance with the above mentioned operating procedure. The pulse width is 40 ms. The potential vs. time wave form of a normal pulse applied upon the monitored area is shown in FIG. 4 wherein tp, T and Eh denote pulse width, pulse standby time and step-up potential, respectively, and the symbols "o" on the curve denote sampling points in which the current for electrolysis at the applied potential and pulse width is sampled.

Each of the measuring points represented at "o", and ".●" in FIG. 3 corresponds to each sampling point in which the electrolytic current at each potential and pulse width is sampled. The curves which are derived from the symbols "o" and " ● " are results of measurement of a reference sample and a welding heat affected portion of the ICM housing, i.e. an object to be monitored. FIG. 3 shows that the welding heat affected portion of the CM housing has a lower anodic electrolytic current in comparison with that of a reference sample which is provided with a sufficient safety factor and has no problem with safety of the object to be monitored. Data of the reference sample are preliminarily inputted to the computer system of the pulse electrochemical instrumentation system. The period of time which is taken to conduct the present electrochemical measurement is about 1 minute. The reference samples represented by symbols "o" are sensitized samples in which carbides are formed by heating at 650° C. for 5 hours so that intergranular stress corrosion cracks are readily formed.

Embodiment 2

Figure 5:
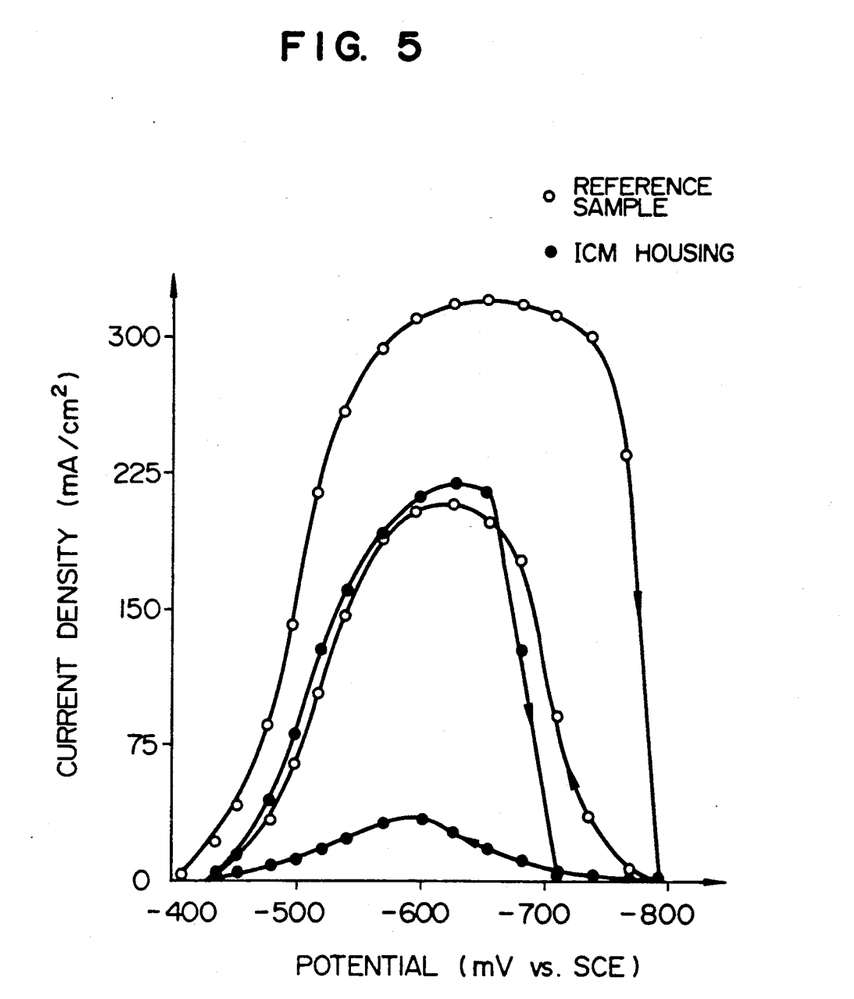
FIG. 5 is a normal pulse voltammogram in forward and return paths in the ICM housing.

FIG. 5 is a graph showing a result which is obtained at a welding heat affected portion of the ICM housing by forward and return paths of a normal pulse. The curves represented by symbols "o", and " ● " show the measurement results of a reference sample and a welding heat affected portion of the ICM housing, respectively. The pulse width is 80 ms. Immobilization behavior in which current abruptly decreases which is shown in FIG. 5 is observed in both the reference sample and the monitored object when the pulse is swept at this pulse width. Reactivation behavior is observed in the return path similarly to the usual EPR measurement. Also in the present embodiment, the ratio of the peak anodic current of the welding heat affected portion of the ICM housing in the return path to that in the forward path is lower than that of the reference sample represented by the symbol "o". It is also apparent from the drawing that the total charge passed in electrolysis (Coulomb number) is also lower. Accordingly, it is shown that the welding heat affected portion of the ICM housing apparently has a lower anodic electrolytic current and a lower total charge passed in electrolysis than those of the reference sample for which a higher safety factor is expected and thus the monitored object has no problem with safety. Data on the reference sample are preliminarily inputted to the computer system of the pulse electrochemical instrumentation system. The period of time required to conduct the present electrochemical measurement per se is about 2 minutes.

Embodiment 2

Figure 6:
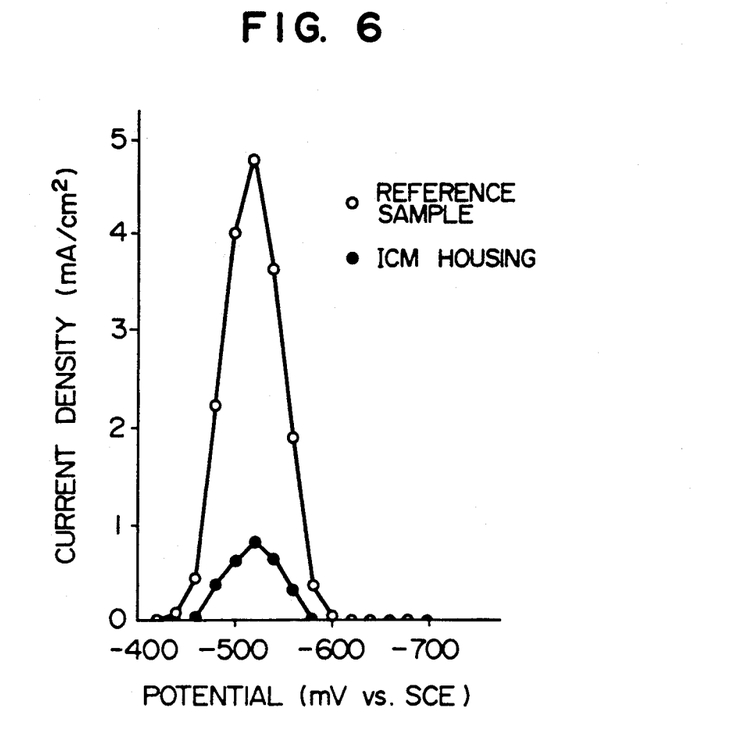
FIG. 6 is a square wave voltammogram in the ICM housing.
Figure 7:
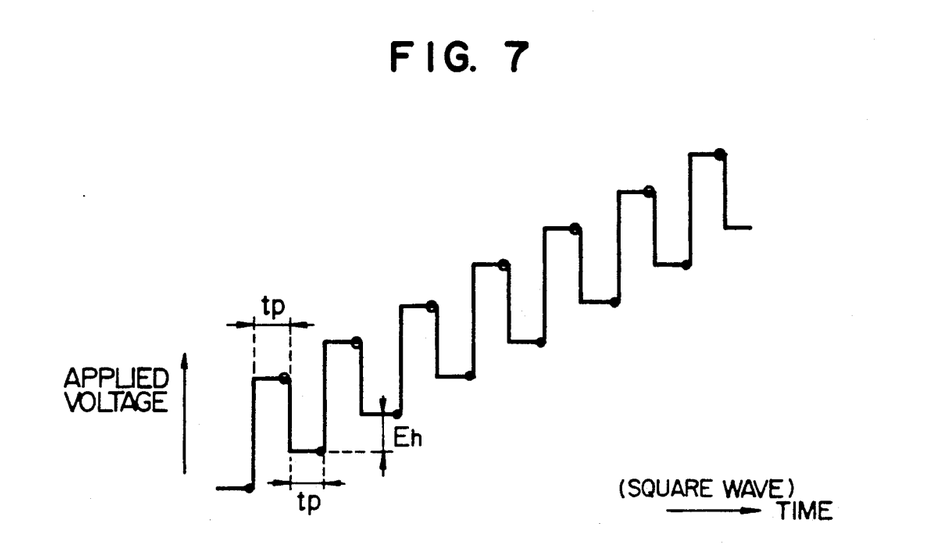
FIG. 7 is a wave form chart showing the relation between potential and time of the square wave.

In this embodiment, the sensitization is measured in the ICM housing by square wave voltammetry. The potential vs time waveform in the square wave voltammetry is shown in FIG. 7, wherein tp and Eh denote pulse width and step-up potential, respectively. Reference symbols "o" and " ● " denote sampling points at which the electrolytic current flowing at each preset pulse potential and pulse width is sampled. In the case of square wave voltammetry, a current plotted through the symbol "o" minus a current plotted through the symbol " ● ", i.e. a change in step-up potential can be determined. Accordingly, in a system having a high anodic current, the current value which is output as a result of the square wave voltammetry is high, similarly to the normal pulse voltammetry. FIG. 6 is a square wave voltammogram result which is measured in the ICM housing. The curves represented with the symbols "o" and " ● " show the measurement results of a reference sample and a welding heat affected portion of the ICM housing, respectively. The pulse width is 40 ms. As is apparent from the drawing, the peak anodic current of the welding heat affected portion of the ICM housing is lower than that of the reference sample represented by the symbol "o". Accordingly, it is shown that the welding heat affected portion of the ICM housing apparently has a lower anodic electrolytic current than that of the reference sample for which a high safety factor is expected, and thus the monitored object has no problem with safety. The period of time required to conduct the present electrochemical measurement per se is about 1 second.

Since the sensitization of the plant structural members can be measured and evaluated by a compact electrochemical cell on a remote control basis for a short period of time in accordance with the present invention, measuring of the sensitization in smaller pipes and the like which has heretofore been hard to perform can be performed. Since the safety of plant structural members can be quickly detected in a broader range, plant operation management can be achieved on a more sophisticated basis.

Embodiment 4

Installation position, structure of a triode system, sensitization measuring system, water quality control system, and stability diagnosing system, in a BWR nuclear reactor pressure vessel will be described by way of the present embodiment.

In a system of the present invention, it is preferable to provide a potentiostat as a means for applying a voltage-time wave form signal upon a working electrode of an electrolytic cell and a CPU for inputting the waveform signal to the potentiostat. The CPU preferably comprises a signal input unit for inputting to said potentiostat a voltage-time waveform signal having given parameters determined by the kind of voltammetry, a storage unit for storing in memory a result of the voltammetry obtained by the execution of the potentiostat in accordance with the relation between the electrolytic current and the potential at which the electrolytic current is obtained; a current value determining unit for processing the data stored in the storing unit for determining a current value or a peak current value which is determined by the kind of the voltammetry; and an operational unit for controlling the concentration of a chemical species to be analyzed based upon the determined current value or peak current value.

The potentiostat performs the function of applying with fidelity the voltage-time waveform inputted from the CPU to a working electrode.

In a system for controlling the quality of coolant, it is preferable to provide a unit for comparing a result of the concentration controlling unit in the CPU with a reference value. It is preferable that this comparing unit be included in the CPU.

Since a voltammetric apparatus, in particular a system for a pulse voltammetric apparatus which is interfaced with a computer operated processing control apparatus, performs a print-out and display of a measurement result, it can clearly notify plant operating personnel of the result of diagnosis of coolant quality. Accordingly, they can monitor the quality of coolant.

Various reference values which are preliminarily inputted to the voltammetric apparatus system can be compared with the analyzed results and inputting and outputting of core coolant quality adjusting gasses and chemical species into the core coolant can be performed in a fast and precise manner based upon the result of comparison.

A primary cooling system of the reactor preferably comprises means for measuring the ion concentrations of $SO_4^{2-}$, $SO_3^-$, $Cl^-$, and $Na^+$ ions which are products of decomposition of reactor purifying chemical resins and alarm means for indicating when at least one of the ion concentrations exceeds a reference value.

Figure 8:
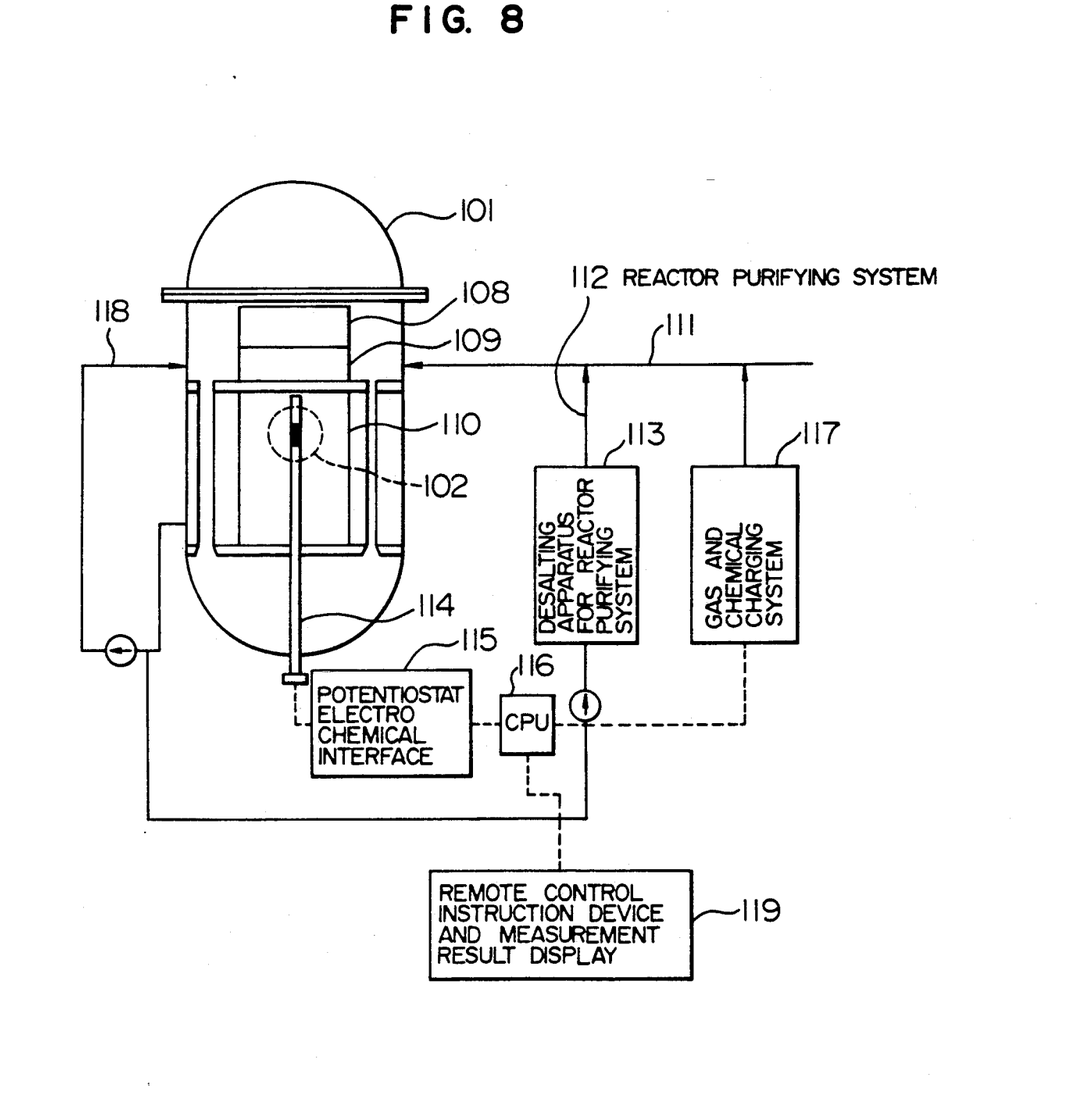
FIG. 8 is a schematic diagram showing a water quality control system for a BWR plant having a triode system in an instrumentation pipe in a nuclear power plant reactor.
Figure 9:
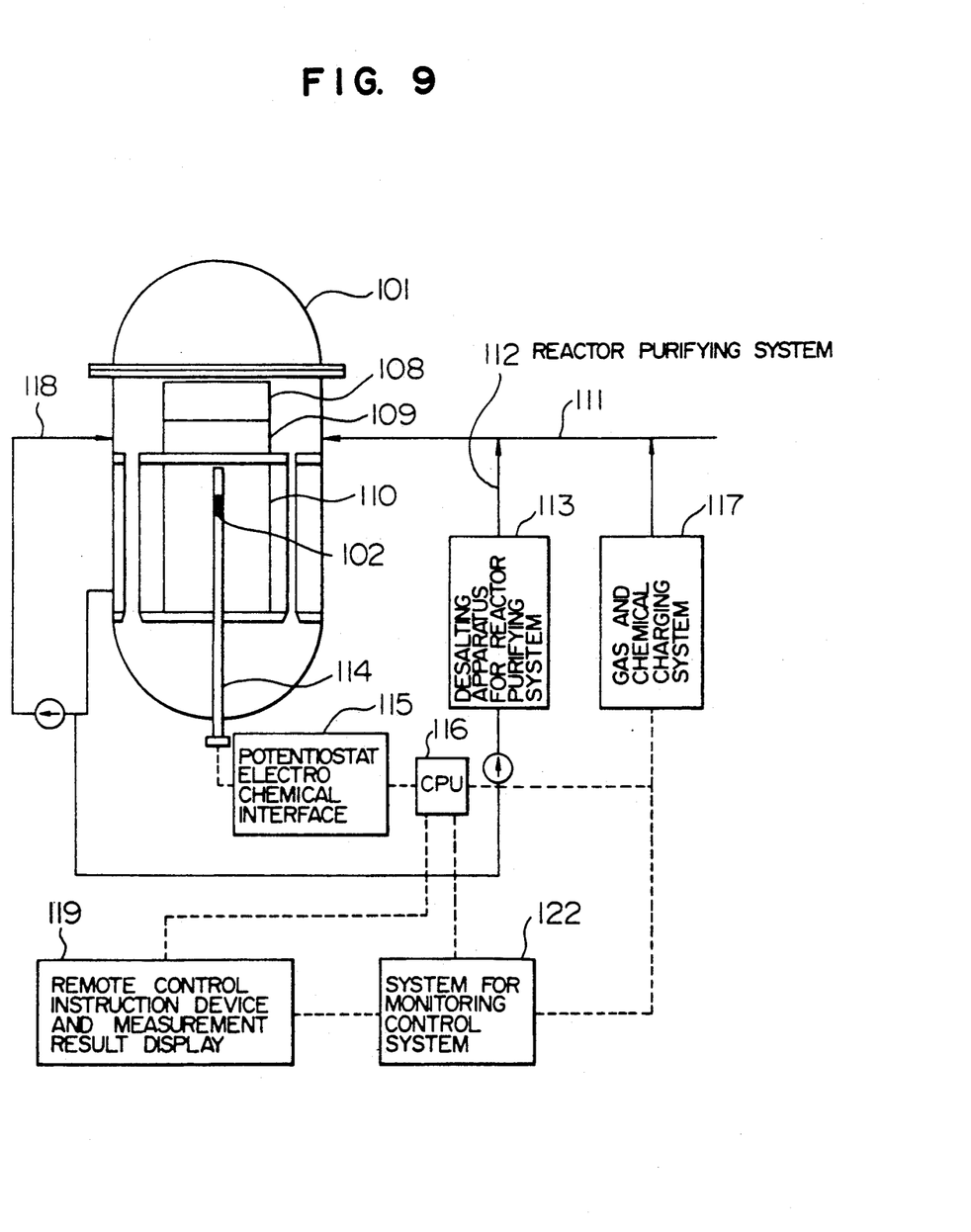
FIG. 9 is a schematic diagram showing a safety diagnosing control system in a nuclear power plant reactor.
Figure 10:
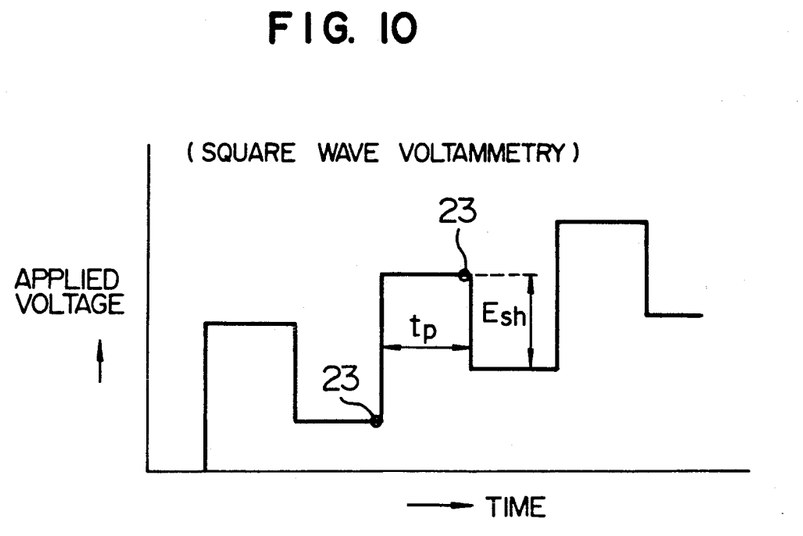
FIGS. 10, 11, 12, and 13 are wave form charts of applied signals in various voltammetries.
Figure 11:
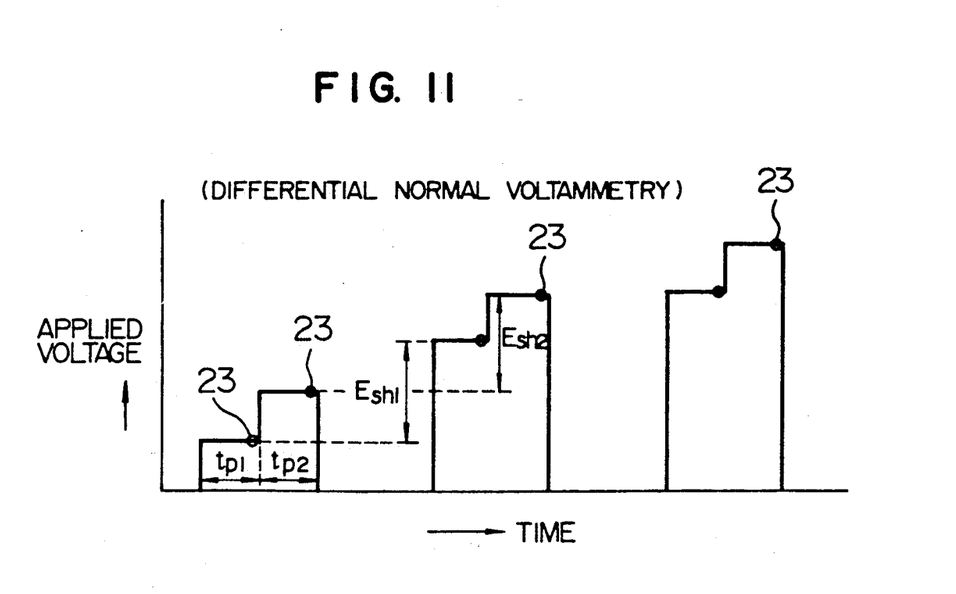
Figure 12:
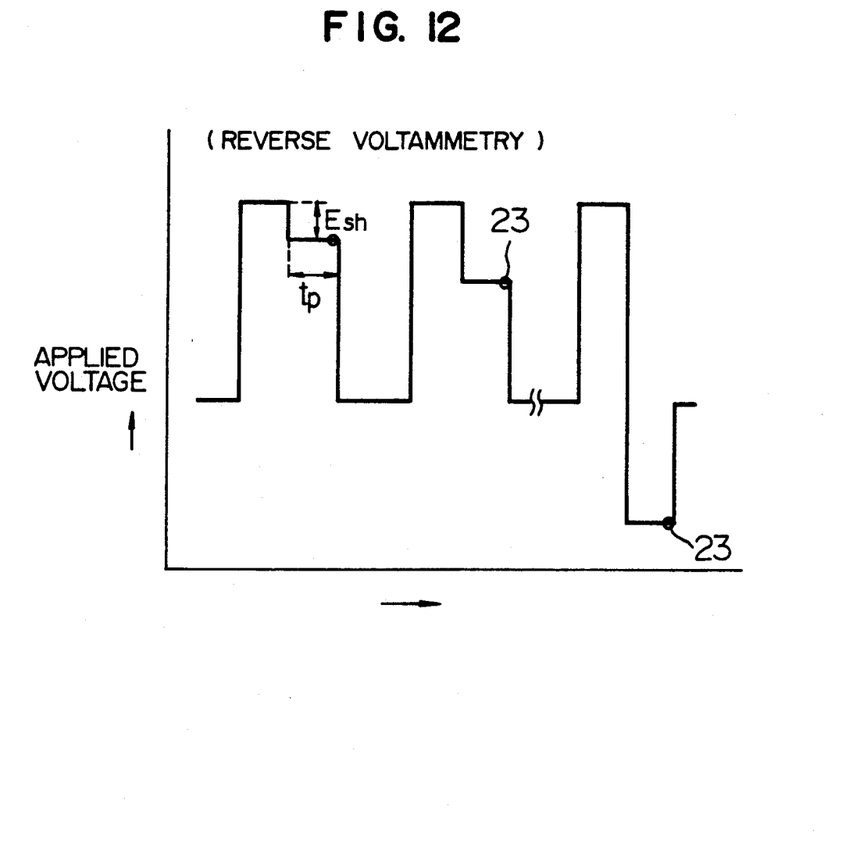
Figure 13:
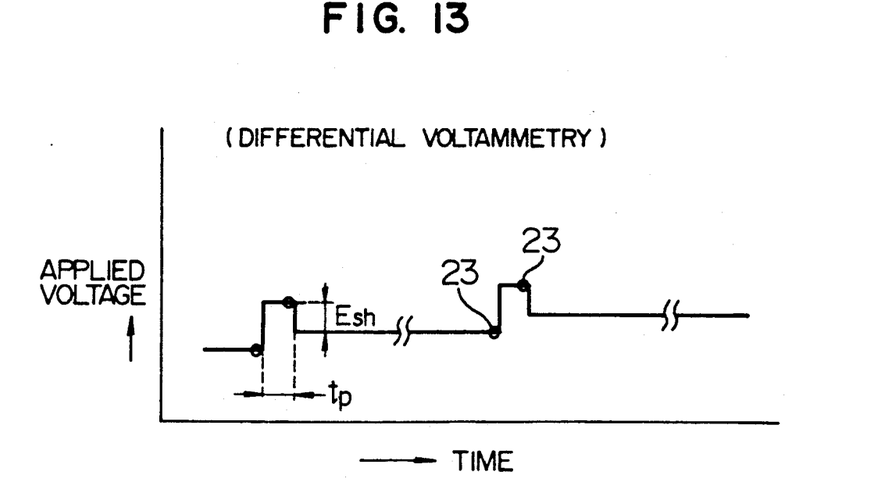

In the present embodiment, the installation position and structure of a triode system in a BWR reactor pressure vessel and the principle of a sensitization measuring system, coolant quality, coolant quality control system and a stabilization diagnosing system, when the reactor is shut down are shown in FIGS. 8 and 9.

FIG. 8 shows structural components associated with the pressure vessel of a BWR reactor. The electrode housing is identical with that of the above mentioned example 1. A triode housing 102 is inserted in an in-core instrumentation pipe 114 and is provided in a portion shown in the drawing of a core 110. In the drawing, reference numeral 101 denotes a reactor pressure vessel; 102 the electrode housing; 108 a drier; 109 a separator; 110 the core; 111 a reactor coolant supply pipe; 112a reactor purifying system; 113 a desalting apparatus for the reactor purifying system; 114 an in-core instrumentation pipe; 115 a potentiostat and electrochemical interface; 116 a CPU; 117 a gas and chemical charging system; 118 a reactor coolant recirculating pipe; and 119 a remote control instruction device and a display for displaying a measurement result. The monitor (working) electrode of triode 102 is operated by the potentiostat, the electrochemical interface 115 and the CPU (computer operated processing and automatic control apparatus) 116.

The result of measurement is fed to the remote control instruction device and measurement result display 119. The measurement result is compared with the preliminarily inputted reference value in the CPU 116. An instruction is fed to a control system of the gas and chemical charging system 117 for opening and closing a valve. This operation is repeated for controlling the coolant quality. The reference electrode may be a saturated calomel electrode (SCE), a standard hydrogen electrode (SHE), a silver-silver chloride electrode (Ag-AgCl), etc. A dotted line in the drawing represents wiring of electrical circuits and interface bus lines, etc.

The electrodes may be disposed on the drier, the separator, an irradiation test piece loading jig, and other removable devices or components located within the reactor pressure vessel. The electrodes may also be directly disposed on the wall of the pressure vessel.

A reactor shown in FIG. 9 is substantially similar with the BWR reactor including electrodes and the electrolytic cell shown in FIG. 1 except that a monitoring control system 122 for monitoring the water quality is added. The monitoring control system 122 has at least one computer operating and processing device. The computer determines whether or not the CPU 116 for controlling the water quality control system and the electrochemical interface are operating normally in order to provide the water quality control system with high reliability and stability.

Signals from the water quality control system including the electrochemical interface 115, the CPU 116, and the gas and chemical charging system 117 are returned to a dummy circuit. Diagnosis whether abnormal operation is detected or not is made by determining whether or not the operating result of the signals, measurement result and the control result are within predetermined ranges of values and precision.

The measurement results are processed in the potentiostat electrochemical interface 115 and the CPU (computer operation and processing device, automatic control apparatus) 116 and the processed results are compared with reference values to control the gas and chemical charging system 117 for controlling the water quality.

Among the various pulse voltammetries, those which obtain current values include, for example, reverse pulse voltammetry as well as normal pulse voltammetry.

The pulse voltammetries which obtain peak current values include differential normal pulse voltammetry and square wave pulse voltammetry as well as differential pulse voltammetry.

The voltage-time waveform signals of several types of pulse voltammetry are shown in FIGS. 10 to 13.

In accordance with the present invention, the pulse electrochemical measurement enables a micro electrochemical measuring cell to be designed. Therefore, rigid detection and measurement of sensitization on an inner surface of small pipe is made possible. A safety maintenance technique which is important for the management of plant operation can be obtained.

We claim:

1. A method of electrochemically measuring the sensitization of a structural member corresponding to the intergranular stress corrosion cracking susceptibility of the structural member, comprising the steps of:

applying a series of potential pulse signals from an electrochemical measurement system to an area of said structural member within an electrochemical cell in a system to be monitored;

measuring the current generated by electrochemical reaction of the structural member in the system to be monitored due to application of each potential pulse signal; and determining the sensitization of the structural member corresponding to the intergranular stress corrosion cracking susceptibility of the structural member on the basis of the obtained current-potential curve.

2. A method of measuring the sensitization of a structural member as defined in claim 1 in which said potential pulse signals are potential signals in a pulse voltammetric mode which is selected from a normal pulse, a square wave, a differential pulse, and a reverse pulse.

3. A method of measuring the sensitization of a structural member as defined in claim 1, in which said determination on the basis of the current-potential curve includes comparing a peak current value on a current-potential curve which is obtained when the potential is swept in a cathodic or anodic direction from a starting potential at which series of pulse potential signals are applied the pulse voltammetry, or a charge passed in electrolysis until a preset potential of the current-potential curve, or a current value at a potential in interest on the current-potential curve with at least one of the current value on the current-potential curve of a sensitized member which is a predetermined reference, or the charge passed in electrolysis or the current value at said potential.

4. A method of measuring the sensitization of a structural member as defined in claim 1 in which said determination on the basis of the current-potential curve includes comparing at least one of the ratio of the peak current values corresponding to the current-potential curves which are obtained when the potential is swept in anodic and cathodic directions from a starting potential at which a series of potential pulse signals including the pulse voltammetry are applied, the ratio of current values on the current-potential curves in respective sweeping directions at potentials in interest, and the ratio of the charges passed in electrolysis corresponding to respective current-potential curves obtained by respective pulse potential sweeping in anodic and cathodic directions with one of the ratio of peak current values obtained from a sensitized material which will become a predetermined reference, the ratio of current values of the current-potential curves in respective sweeping directions at a potential in interest, and the ratio of charges passed in electrolysis corresponding to the current-potential curves in respective sweeping directions.

5. A method of measuring the sensitization of a structural member as defined in claim 1 in which said electrochemical cell includes an on-line monitor mechanism for positioning the electrochemical cell in an object to be monitored, an operation control mechanism using a magnetic force or a vacuum control mechanism, a remote control operating unit, or pipes for charging or discharging a measuring electrolyte and a liquid for washing the object after measurement, and a remote control system for positioning said electrochemical cell on the object to be monitored is provided.

6. A method of measuring the sensitization of a structural member as defined in claim 1 in which an electrochemical measuring system is used which is capable of repeatedly sweeping the pulse potential in anodic and cathodic directions from a starting potential at which a series of pulse potential signals including pulse voltammentry are applied and includes a system which is capable of measuring the charge passed in electrolysis or automatically reading the current value on a current-potential ,curve at a preset potential to display measured data on a CRT or to output data.

7. A method of electrochemically measuring the sensitization of a structural member corresponding to the intergranular stress corrosion cracking susceptibility of the structural member, comprising the steps of:
applying a series of potential pulse signals from an electrochemical measurement system to an area of said structural member within an electrochemical cell in a system to be monitored;
measuring the current generated by electrochemical reaction of the structural member in the system to be monitored due to application of each potential pulse signal; and
determining the sensitization of the structural member corresponding to the intergranular stress corrosion cracking susceptibility of the structural member on the basis of the amount of charge passed in electrolysis.

8. A system for controlling the water quality in a coolant system of a nuclear power plant, comprising:
an electrode housing for an electrolytic cell adapted to be disposed within a structural member which is in contact with coolant or on a structural member of a reactor pressure vessel;
a signal applying unit for applying a voltammetry voltage-time wave form signal having given parameters concerned with the electrochemical potential of the structure member versus a reference electrode potential;
a signal inputting unit for inputting a voltage-time waveform signal having said parameters determined by the type of voltammetry to said signal applying unit;
a unit for storing in a memory the results of the voltammetry executed based upon the signal from said signal applying unit on the basis of the relation between the electrolytic current and the potential at which the current for electrolysis is obtained;
a current determining unit for processing data stored in said storing unit to determine a current or peak current depending upon the type of voltammetry;
an operating unit for determining the sensitization of said structural member based upon the determined current or peak current; and
coolant control means for controlling the quality of said coolant based upon the information from said operating unit.

9. A system for controlling the water quality in a coolant system of a nuclear power plant as defined in claim 8, in which the signal which is input to said signal applying unit comprises a pulsed voltage-time wave form signal.

10. A system for controlling the water quality in a coolant system of a nuclear power plant as defined in claim 8, in which said coolant quality control means includes means for controlling the amount of hydrogen charged into a primary coolant system.

11. A system for controlling the water quality in a coolant system of a nuclear power plant as defined in claim 8, in which said coolant quality control means includes means for controlling the amount of hydrazine charged into a steam generator in a core.

12. A system for controlling the coolant quality in a coolant system of a nuclear power plant as defined in claim 8, further including a function generator between said signal applying unit and said signal input unit wherein the waveform signal from said signal input unit is input to said signal applying unit via said function generator.

13. A system for controlling the water quality in a coolant system of a nuclear power plant, comprising:
an electrode housing for an electrochemical cell positioned within a structural member which is in contact with coolant or no a structural member of a reactor pressure vessel;
a signal applying unit for applying a voltammetry voltage-line waveform signal having given parameters concerned with the potential of the structural member versus a reference electrode potential;
a signal inputting unit for inputting a voltage-time waveform signal have said parameters determined by the type of voltammetry to said signal applying unit;

a unit for storing in a memory the results of the voltammetry executed based upon the signal from said signal applying unit on the basis of the relation between the current for electrolysis and the potential at which the electrolyzing current is obtained;

a current determining unit for processing data stored in said storing unit to determine a current or peak current depending upon the type of voltammetry;

an operating unit for determining the sensitization of said structural member based upon the determined current or peak current;

a comparing unit for comparing a result of said operating unit with a reference value; and a coolant control means for controlling the quality of said coolant based upon information on a result of comparison from said comparing wall.

14. A system for controlling the water quality in a coolant system in a nuclear power plant as defined in claim 13, further including a system for monitoring whether or not said signal input unit, said signal applying unit, said operation unit and said comparing unit are operating normally.

15. A preventive safety system for a nuclear power plant, comprising:

an electrode housing for an electrochemical cell adapted to be positioned within a structural member which is in contact with coolant or on a structural member of a reactor pressure vessel;

a signal applying unit for applying a voltammetry voltage-time waveform signal having given parameters concerned with the potential of the structural member versus a reference electrode potential;

a signal inputting unit for inputting a voltage-time waveform signal having said parameters determined by the type of voltammetry to said signal applying unit;

a unit for storing in a memory the results of the voltammetry executed based upon the signal from said signal applying unit on the basis of the relation between the electrolytic current and the potential at which the electrolyzing current is obtained;

a current determining unit for processing data stored in said storing unit to determine a current or peak current depending upon the type of voltammetry;

p1 an operating unit for determining the sensitization of said structural member based upon the determined current or peak current;

a comparing unit for comparing a result of said operating unit with a reference value; and means for sending an alarm when said comparing means determines that the result from said concentration operating unit exceeds said reference value.

16. A preventive safety system for a nuclear power plant, comprising:

an electrode housing for an electrolytic cell disposed within a structural member which is in contact with coolant or on a structural member of a reactor pressure vessel;

a signal applying unit for applying a voltammetry voltage-time waveform signal having given parameters concerned with the potential of the structural member versus a reference electrode potential;

a signal inputting unit for inputting a voltage-time waveform signal having said parameters determined by the type of voltammetry to said signal applying unit;

a unit for storing in a memory the results of the voltammetry executed based upon the signal from said signal applying unit on the basis of the relation between the electrolytic current and the potential at which the electrolyzing current is obtained;

a current determining unit for processing data stored in said storing unit to determine a current or peak current depending upon the kind of the voltammetry;

an operating unit for determining the sensitization of said structural member based upon the determined current or peak current; and a comparing unit for comparing a result of said operating unit with a reference value; wherein occurrence of an accident in a coolant system is predicted based upon information from said comparing unit.

17. A preventive safety system for a nuclear power plant as defined in claim 16 further including means for sensing an alarm when said monitoring system detects an abnormality in operation.

18. A system for controlling the quality of high temperature and high pressure water based upon a result which is obtained by detecting the sensitization of a structural member to intergranular stress corrosion cracking in a boiling water nuclear reactor, a pressurized water nuclear reactor or a thermal power generating plant, comprising:

an electrode housing for an electrochemical cell adapted to be positioned within a structural member which is in contact with coolant or on a structural member of a reactor pressure vessels;

a signal applying unit for applying a voltage-time waveform signal having given parameters concerned with the potential of the structural member versus reference electrode potential;

a signal inputting unit for inputting a voltage-time waveform signal having parameters determined by the type of voltammetry to said signal applying unit;

a unit for storing in a memory the results of the voltammetry executed based upon the signal from said signal applying unit on the basis of the relation between the electrolytic current and the potential at which the electrolyzing current is obtained;

a current determining unit for processing data stored in said storing unit to determine a current or peak current depending upon the type of voltammetry;

an operating unit for determining the sensitization of said structural member based upon the determined current or peak current; and control means for controlling the water quality of said coolant based upon information from said operating unit.

* * * * *